(12) United States Patent
Terazaki et al.

(10) Patent No.: US 7,754,195 B2
(45) Date of Patent: Jul. 13, 2010

(54) HAIR CLEANSING COMPOSITIONS

(75) Inventors: Hiroyuki Terazaki, Tokyo (JP); Fumiko Kasuga, Tokyo (JP); Osamu Hirota, Tokyo (JP)

(73) Assignee: Kao Corporation, Tokyo (JP)

( * ) Notice: Subject to any disclaimer, the term of this patent is extended or adjusted under 35 U.S.C. 154(b) by 1182 days.

(21) Appl. No.: 10/337,737

(22) Filed: Jan. 8, 2003

(65) Prior Publication Data

US 2003/0170197 A1 Sep. 11, 2003

(30) Foreign Application Priority Data

Jan. 21, 2002 (JP) .............................. 2002-011922

(51) Int. Cl.
*A61Q 5/02* (2006.01)
(52) U.S. Cl. .............. 424/70.24; 424/70.11; 424/70.12; 424/70.19
(58) Field of Classification Search ........................ None
See application file for complete search history.

(56) References Cited

U.S. PATENT DOCUMENTS

| | | | |
|---|---|---|---|
| 5,137,715 A * | 8/1992 | Hoshowski et al. ...... | 424/70.17 |
| 5,403,517 A * | 4/1995 | Horinishi et al. ......... | 424/70.21 |
| 6,056,947 A | 5/2000 | Kahre et al. | |
| 6,074,996 A | 6/2000 | Elliott et al. | |
| 6,555,101 B1 | 4/2003 | Kahre et al. | |

FOREIGN PATENT DOCUMENTS

| | | |
|---|---|---|
| DE | 100 05 162 A1 | 8/2001 |
| EP | 0 511 652 A1 | 11/1992 |
| EP | 0 627 216 | 12/1994 |
| EP | 1 118 319 A1 | 7/2001 |
| EP | 1 123 693 A2 | 8/2001 |
| EP | 1 329 215 | 7/2003 |
| EP | 1 340 488 | 9/2003 |
| JP | 6-172131 | 6/1994 |
| JP | 7-48236 | 2/1995 |
| JP | 8-505601 | 6/1996 |
| JP | 11-199446 | 7/1999 |
| JP | 2001-10935 | 1/2001 |
| JP | 2003-513996 | 4/2003 |
| WO | WO 92/10162 | 6/1992 |
| WO | WO 98/19656 * | 5/1998 |
| WO | 99/51193 | 10/1999 |
| WO | WO 01/35905 A2 | 5/2001 |
| WO | WO 03/028682 | 4/2003 |
| WO | WO 03/032935 | 4/2003 |

OTHER PUBLICATIONS

U.S. Appl. No. 10/337,774, filed Jan. 8, 2003, Terazaki, et al.
As expertise: Product Data Sheet, "Texapon N 70", Dec. 5, 1997, 1 page.
As expertise : Product Data Sheet, "Gluadin W 40", Feb. 1995, 1 page.
As expertise : Product Data Sheet, "Lanette O", from 3-4 1997, 1 page.
As expertise : Product Data Sheet, "Plantaren 818 UP", Dec. 1995, 2 pages.
As expertise: excerpt from the book: Fey/Otte: "Wörterbuch der Kosmetik", 4th ed., Wissenschaftliche Verlagsgesellschaft mbH Stuttgart, 1997; cover page and pp. 213 and 36 (with partial English translation).
Handbuch der Konservierungsmittel, Verlag für chemische Industrie, H. Ziolkowsky GmbH, D-86150 Augsburg, 4 pages (1995).

* cited by examiner

*Primary Examiner*—Jyothsna A Venkat
(74) *Attorney, Agent, or Firm*—Oblon, Spivak, McClelland, Maier & Neustadt, L.L.P.

(57) ABSTRACT

To provide a hair cleansing composition having good foamability and high-lubricity foam quality upon washing and smooth touch upon rinsing, and providing excellent feeling in use.

20 Claims, No Drawings

HAIR CLEANSING COMPOSITIONS

TECHNICAL FIELD

This invention relates to hair cleansing compositions, which have good foamability and high-lubricity foam quality upon washing and smooth touch upon rinsing.

BACKGROUND ART

Washing of hair with a hair cleansing composition such as a shampoo is conducted to remove dirt, impurities or extraneous matter adhered on the hair. Hair damaged by hair coloring treatment or permanent wave treatment is, however, susceptible to further damage because the hair rubs against each other and tangles with each other during washing. To permit hair washing without tangling even in the case of damaged hair, combined use of various surfactants or addition of polymers is therefore performed. With these techniques, however, fully satisfactory performance has not been obtained yet with respect to foamability and foam lubricity upon washing and smoothness upon rinsing.

DISCLOSURE OF THE INVENTION

The present invention has as an object the provision of a hair cleansing composition, which has good foamability and high-lubricity foam quality upon washing and smooth touch upon rinsing, and is excellent in use feeling.

The present inventors have found that combined use of a sulfate-type anionic surfactant, a higher alcohol having a particular chain length and a cationic polymer makes it possible to obtain a hair cleansing composition having the above-described properties, especially high-lubricity foam quality.

Described specifically, the present invention provides a hair cleansing composition comprising the following ingredients (A) to (C):

(A) an anionic surfactant having a sulfate group,
(B) a higher alcohol having 10 to 14 carbon atoms, and
(C) a cationic polymer;
wherein the hair cleansing composition has a pH of from 3 to 5.5 when diluted 20-fold by weight with water.

Owing to the above-described features, the hair cleansing composition according to the present invention has good foamability and high-lubricity foam quality upon washing and smooth touch upon rinsing, and is excellent in use feeling.

BEST MODES FOR CARRYING OUT THE INVENTION

Examples of the sulfate-type anionic surfactant as the ingredient (A) can include polyoxyethylene alkyl ether sulfates, polyoxyethylene alkenyl ether sulfates, alkyl sulfates, and polyoxyalkylene alkyl phenyl ether sulfates. Particularly preferred are those represented by the following formula (1) or (2):

$$R^1O(CH_2CH_2O)_mSO_3M \quad (1)$$

$$R^2OSO_3M \quad (2)$$

wherein $R^1$ represents an alkyl group or alkenyl group having 10 to 18 carbon atoms, $R^2$ represents an alkyl group having 10 to 18 carbon atoms, M represents an alkali metal, alkaline earth metal, ammonium, alkanolamine or basic amino acid, and m stands for a number of from 1 to 5.

Two or more of these sulfates may be used in combination as the ingredient (A). From the standpoint of foamability and also of liquid properties and cleansing property at the time of use, the content of the ingredient (A) may range preferably from 1 to 50 wt. %, more preferably from 8 to 30 wt. %, particularly from 10 to 22 wt. %, all based on the hair cleansing composition according to the present invention.

Preferred examples of the higher alcohol having the carbon number of from 10 to 14, the ingredient (B), are those containing linear or branched, particularly linear alkyl groups having the carbon numbers of from 12 to 14. More specific examples can include decyl alcohol, lauryl alcohol and myristyl alcohol, with myristyl alcohol being particularly preferred.

Two or more of these higher alcohols may be used in combination as the ingredient (B). From the standpoints of making improvements in finish, stability and foam lubricity, the content of the ingredient (B) may range preferably from 0.05 to 5 wt. %, more preferably from 0.1 to 3 wt. %, particularly from 0.5 to 2 wt. %, all based on the hair cleansing composition according to the present invention.

Examples of the cationic polymer as the ingredient (C) can include cationic cellulose derivatives, cationic starch, cationic guar gum derivatives, homopolymer of diallyl quaternary ammonium salt, diallyl quaternary ammonium salt/acrylamide copolymer, quaternized polyvinylpyrrolidone derivatives, polyglycol polyamine condensation products, vinylimidazolium trichloride/vinylpyrrolidone copolymer, hydroxyethylcellulose/dimethyldiallylammonium chloride copolymer, vinylpyrrolidone/quaternized dimethylaminoethyl methacrylate copolymer, polyvinylpyrrolidone/alkyl aminoacrylate copolymer, polyvinylpyrrolidone/alkyl aminoacrylate/vinyl caprolactam copolymers, vinylpyrrolidone/methacrylamidopropyl trimethylammonium chloride copolymer, alkylacrylamide/acrylate/alkylaminoalkylacrylamide/polyethylene glycol methacrylate copolymers, adipic acid/dimethylaminohydroxypropyl ethylenetriamine copolymer ("Cartaretin"; product of Sandoz Chemicals Corp., U.S.A.), and cationic polymers disclosed in JP-A-53139734 and JP-A-60036407. Particularly preferred are cationic cellulose derivatives and cationic guar gum derivatives.

Two or more of these cationic polymers may be used in combination as the ingredient (C). From the standpoint of foam lubricity and also of smoothness from washing to rinsing, the content of the ingredient (C) may range preferably from 0.05 to 5 wt. %, more preferably from 0.1 to 3 wt. %, particularly from 0.3 to 1 wt. %, all based on the hair cleansing composition according to the present invention.

The weight ratio of the sulfate-type anionic surfactant (A) to the higher alcohol (B) may range preferably from 10/1 to 40/1, while the weight ratio of the higher alcohol (B) to the cationic polymer (C) may range preferably from 10/1 to 10/10.

To further improve the foamability of the hair cleansing composition according to the present invention, one or more surfactants other than the ingredient (A), said surfactants being selected from anionic surfactants, nonionic surfactants and amphoteric surfactants, may also be incorporated.

The anionic surfactants other than the ingredient (A) can include sulfonate-type anionic surfactants and carboxylate-type anionic surfactants. Illustrative are alkyl sulfosuccinate salts, alkyl polyoxyalkylene sulfosuccinate salts, higher fatty acid salts, and alkanesulfonate salts.

Examples of the nonionic surfactants can include polyoxyalkylene sorbitan fatty acid esters, polyoxyalkylene sorbitol fatty acid esters, polyoxyalkylene glycerol fatty acid esters, polyoxyalkylene fatty acid esters, polyoxyalkylene alkyl ethers, polyoxyalkylene alkyl phenyl ethers, polyoxyalkylene (hydrogenated) castor oils, sucrose fatty acid esters, polyglyceryl alkyl ethers, polyglyceryl fatty acid esters, fatty acid alkanolamides, and alkyl glycosides. Among these, alkyl glycosides, polyoxyalkylene ($C_8$-$C_{20}$) fatty acid esters, polyoxyethylene sorbitan fatty acid esters, polyoxyethylene hydrogenated castor oil and fatty acid alkanolamides are preferred. Preferred fatty acid alkanolamides are those containing acyl groups having the carbon numbers of from 8 to 18, especially from 10 to 16. The fatty acid alkanolamides can be either monoalkanolamides or dialkanolamides. Preferred are those containing hydroxyalkyl groups having the carbon numbers of from 2 to 3. Illustrative are oleic diethanolamide, palm kernel oil fatty acid diethanolamide, coconut oil fatty acid diethanolamide, lauric diethanolamide, polyoxyethylene coconut oil fatty acid monoethanolamides, coconut oil fatty acid monoethanolamides, lauric isopropanolamide, and lauric monoethanolamide.

The amphoteric surfactants can include betaine-type surfactants. Among these, betaine-type surfactants such as alkyldimethylaminoacetic acid betaines and fatty acid amidopropyl betaines are more preferred, with fatty acid amidopropyl betaines being particularly preferred. Of these fatty acid amidopropyl betaines, preferred are those having acyl groups whose carbon numbers are from 8 to 18, especially from 10 to 16. Particularly preferred are lauramidopropyl betaine, palm kernel oil fatty acid amidopropyl betaines, and coconut oil fatty acid amidopropyl betaines.

These surfactants other than the ingredient (A) can be incorporated, as needed, in the hair cleansing composition according to the present invention. When the hair cleansing composition according to the present invention is formulated into the form of an aqueous liquid cleansing composition, use of a fatty acid amidopropyl betaine or fatty acid alkanolamide in combination with the ingredient (A) is particularly preferred because this makes it possible not only to further improve the foaming power but also to obtain adequate liquid properties.

When a fatty acid amidopropyl betaine or fatty acid alkanolamide is incorporated as described above, its content may range preferably from 0 to 10 wt. %, more preferably from 1 to 8 wt. %, particularly from 2 to 6 wt. %, all based on the hair cleansing composition according to the present invention, since good foam-boosting effect can be obtained.

In the hair cleansing composition according to the present invention, a silicone can be incorporated to improve the post-drying finish. Examples of the silicone can include the followings:

(1) Dimethylpolysiloxanes
Illustrative are those represented by the following formula:

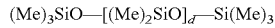

wherein each Me represents a methyl group, and d stands for a number of from 3 to 20,000.

(2) Amino-Modified Silicones
One having an average molecular weight of from about 3,000 to 100,000 and listed under the name of "Amodimethicone" in the third edition of the CTFA dictionary (Cosmetic Ingredient Dictionary, U.S.A.) is preferred, although a variety of amino-modified silicones are usable. This amino-modified silicone can be used preferably as an aqueous emulsion, and its commercial products include "SM 8704C" (Dow Corning Toray Silicone Co., Ltd.) and "DC 929" (Dow Corning Corporation).

(3) Other Silicones
As silicones other than those described above, there are also polyether-modified silicones, methylphenylpolysiloxane, fatty-acid-modified silicones, alcohol-modified silicones, alkoxy-modified silicones, epoxy-modified silicones, fluorine-modified silicones, cyclic silicones, alkyl-modified silicones, and the like.

Two or more of these silicones may be used in combination. The content of the silicone may range preferably from 0.01 to 20 wt. %, more preferably from 0.1 to 10 wt. %, particularly from 1 to 5 wt. %, all based on the hair cleansing composition according to the present invention.

An organic acid may be incorporated further in the hair cleansing composition according to the present invention to make improvements in hair finish such as luster and manageability. Illustrative of the organic acid are carboxylic acids such as monocarboxylic acids, dicarboxylic acids, hydroxycarboxylic acids and polycarboxylic acids, and alkylphosphoric acids. Among these, carboxylic acids, especially dicarboxylic acids and hydroxycarboxylic acids are preferred. Examples of such dicarboxylic acids can include malonic acid, succinic acid, glutaric acid, adipic acid, maleic acid, fumaric acid and phthalic acid. Examples of such hydroxycarboxylic acids can include glycolic acid, lactic acid, hydroxyacrylic acid, oxybutyric acid, glyceric acid, malic acid, tartaric acid and citric acid. Of these, α-hydroxycarboxylic acids are preferred, with lactic acid and malic acid being particularly preferred.

Two or more of these organic acids may be used in combination. The content of the organic acid may range preferably from 0.05 to 10 wt. %, more preferably from 0.1 to 5 wt. %, particularly from 0.5 to 1 wt. %.

For providing the hair cleansing composition according to the present invention with improved touch feel and also with improved luster after washing, an aromatic alcohol may be incorporated further. Examples of the aromatic alcohol can include benzyl alcohol, benzyloxyethanol and phenoxyethanol, with benzyl alcohol and benzyloxyethanol being particularly preferred.

Two or more aromatic alcohols may be used in combination. The content of the aromatic alcohol may range preferably from 0.01 to 20 wt. %, more preferably from 0.1 to 10 wt. %, particularly form 0.5 to 5 wt. %, all based on the hair cleansing composition according to the present invention.

In addition to the above-described ingredients, ingredients which are employed in ordinary hair cleansing compositions can also be incorporated in the hair cleansing composition according to the present invention as needed depending upon the purpose of use. Such ingredients can include, for example, antidandruff agents; vitamins; anti-inflammatories; chelating agents; humectants such as propylene glycol, glycerin, diethylene glycol monoethyl ether, sorbitol and panthenol; colorants such as dyes and pigments; viscosity controlling agents such as hydroxyethylcellulose, methylcellulose, polyethylene glycol, ethanol, clay mineral, and salts such as sodium chloride; pH adjusters such as potassium hydroxide; plant extracts; pearlants; fragrances; color additives; ultraviolet absorbers; antioxidants; and ingredients described in ENCYCLOPEDIA OF SHAMPOO INGREDIENTS (MICELLE PRESS).

The hair cleansing composition according to the present invention has a pH of from 3.0 to 5.5, preferably from 3 to 4 when diluted 20-fold by weight with water (to the concentration upon application to hair).

The form of the hair cleansing composition according to the present invention can be chosen as desired, including a liquid form, a powder form, a gel form, and a granular form. However, a liquid form making use of water or a lower alcohol as a solvent, especially water is preferred.

The hair cleansing composition according to the present invention can be formulated into a form for use in a bathroom such as a shampoo composition, a shampoo with rinse, a treatment or a conditioner, with a shampoo composition being particularly preferred.

EXAMPLES

In the following Examples and Comparative Examples, each "pH" indicates a pH as measured when diluted 20-fold by weight with water.

Examples 1-4 and Comparative Examples 1-3

Shampoo compositions shown in Table 1 were prepared, and their organoleptic ranking was conducted.

(Washing Method)

Subsequent to thorough moistening of hair, 5 g or 10 g (5 g for semi-long hair, 10 g for long hair) of a shampoo composition were dispensed, and then, the hair was washed. The hair was rinsed thoroughly and then dried fully with hot air from a dryer.

(Organoleptic Ranking)

Ranking was conducted by five expert panelists in accordance with the following ranking systems, and based on average scores, the shampoo compositions were ranked.

Ranking systems
  (1) Foam volume upon foaming
    4: Foams very well.
    3: Foams well.
    2: Foams to ordinary level.
    1: Does not foam well.
    0: Does not foam.
  (2) Lubricity of foam
    4: Foams have very high lubricity.
    3: Foams have good lubricity.
    2: Foams have some lubricity.
    1: Foams do not have much lubricity.
    0: Foams have not lubricity.
  (3) Fineness of foams
    4: Foams are very fine.
    3: Foams are fine.
    2: Foams are rather fine.
    1: Foams are rather coarse.
    0: Foams are coarse.
  (4) Smoothness upon rinsing
    4: Very smooth.
    3: Smooth.
    2: Slightly smooth.
    1: Not smooth.
    0: Not smooth at all.
  (5) Softness of hair after drying
    4: Very soft.
    3: Soft.
    2: Slightly soft.
    1: Not soft.
    0: Not soft at all.
  (6) Luster of hair after drying
    4: Pronounced improvement in luster is observed.
    3: Improvement in luster is observed.
    2: Some improvement in luster is observed.
    1: No improvement in luster.
    0: Luster is lost.

Ranking
  A: Average ranking score ≧ 3.5
  B: 3.5 > Average ranking score ≧ 2.5
  C: 2.5 > Average ranking score ≧ 1.5
  D: 1.5 > Average ranking score

TABLE 1

| | Examples | | | | Comparative Examples | | |
|---|---|---|---|---|---|---|---|
| | 1 | 2 | 3 | 4 | 1 | 2 | 3 |
| Ingredients (wt. %) | | | | | | | |
| (A) | | | | | | | |
| Sodium POE(2) lauryl ether sulfate | 10 | 15 | 10 | 10 | 10 | 15 | 10 |
| Sodium lauryl sulfate | 5 | — | 5 | — | 5 | — | 5 |
| (B) | | | | | | | |
| Myristyl alcohol | 1 | 1 | 1 | 1 | — | 1 | — |
| (C) | | | | | | | |
| Cationic hydroxyethylcellulose | 0.5 | — | 0.3 | — | 0.5 | — | — |
| Cationic guar gum | — | 0.5 | — | 0.5 | — | — | — |
| Others | | | | | | | |
| Lauramidopropyl betaine | — | — | — | 2 | 1 | — | — |
| Cocoyl monoethanolamide | — | — | 1 | — | — | — | 1 |
| Malic acid | — | 0.75 | — | 0.1 | — | 0.75 | — |
| Lactic acid | 0.1 | — | 1 | — | 0.1 | — | 1 |
| Benzyl alcohol | 0.5 | 0.5 | 0.5 | 0.1 | 0.5 | 0.5 | 0.5 |
| Fragrance | Trace | Trace | Trace | Trace | Trace | Trace | Trace |
| Purified water | Bal. | Bal. | Bal. | Bal. | Bal. | Bal. | Bal. |
| pH (when diluted 20-fold by weight) | 5.5 | 3.6 | 3.9 | 5.3 | 5.5 | 3.6 | 3.9 |
| Ranking | | | | | | | |
| Foam volume | A | A | A | A | B | A | C |
| Foam lubricity | A | A | A | A | C | C | C |
| Fineness of foam | A | A | A | A | C | C | C |
| Touch upon rinsing | B | A | B | B | C | C | C |
| Smoothness upon rinsing | B | A | A | A | B | C | C |
| Hair softness after drying | A | A | A | A | B | B | C |
| Hair luster after drying | B | A | A | B | B | B | C |

Example 5

Clear Shampoo

| | (wt. %) |
|---|---|
| Sodium POE(2) lauryl ether sulfate | 10.0 |
| Myristyl alcohol | 0.5 |
| Cationic hydroxyethylcellulose | 0.2 |
| Lauramidopropyl betaine | 0.5 |
| Cocoyl monoethanolamide | 0.3 |
| Malic acid | 0.75 |
| Glycerin | 1.0 |
| Deionized water | Balance |

The above-described shampoo (pH 3.7) was excellent in foam volume upon washing, and also good in foam lubricity upon washing and smoothness upon rinsing.

Example 6

Conditioning Shampoo

|  | (wt. %) |
|---|---|
| Sodium POE(2) lauryl ether sulfate | 8.0 |
| Sodium laurylsulfate | 5.0 |
| Myristyl alcohol | 1.0 |
| Cationic hydroxyethylcellulose | 0.5 |
| Cocoyl monoethanolamide | 0.7 |
| Citric acid | 0.3 |
| Ethylene glycol distearate | 3.0 |
| Glycerin | 1.0 |
| Sodium chloride | 1.0 |
| Deionized water | Balance |

The above-described shampoo (pH 5.5) was excellent in foam volume upon washing, and also good in foam lubricity upon washing and smoothness upon rinsing.

Example 7

Conditioning Shampoo

|  | (wt. %) |
|---|---|
| Sodium POE(2) lauryl ether sulfate | 11.0 |
| Sodium lauryl sulfate | 5.0 |
| Myristyl alcohol | 1.0 |
| Cetanol | 0.5 |
| Cationic hydroxyethylcellulose | 0.3 |
| Cationic guar gum | 0.3 |
| Cocoyl monoethanolamide | 1.0 |
| Dimethicone (polymerization degree: 2,000) | 0.25 |
| Dimethicone (polymerization degree: 200) | 0.25 |
| Malic acid | 0.7 |
| Benzyl alcohol | 0.5 |
| Ethylene glycol distearate | 3.0 |
| Glycerin | 1.0 |
| Sodium chloride | 0.2 |
| Deionized water | Balance |

The above-described shampoo (pH 3.7) was excellent in foam volume upon washing, and also good in foam lubricity upon washing and smoothness upon rinsing.

Example 8

Conditioning Shampoo

|  | (wt. %) |
|---|---|
| Sodium POE(2) lauryl ether sulfate | 8.0 |
| Myristyl alcohol | 1.0 |
| Cetanol | 0.5 |
| Cationic guar gum | 0.3 |
| Lauramidopropyl betaine | 3.0 |
| Malic acid | 0.5 |
| Lactic acid | 0.5 |
| Behenyltrimonium chloride | 0.5 |
| Ethylene glycol distearate | 2.0 |
| Sodium chloride | 1.0 |
| Sodium hydroxide | q.s. to pH 3.9 |
| Deionized water | Balance |

The above-described shampoo was excellent in foam volume upon washing, and also good in foam lubricity upon washing and smoothness upon rinsing.

Example 9

Antidandruff Shampoo

|  | (wt. %) |
|---|---|
| Sodium POE(2) lauryl ether sulfate | 10.0 |
| Sodium lauryl sulfate | 5.5 |
| Myristyl alcohol | 1.0 |
| Cetanol | 0.5 |
| Cationic hydroxyethylcellulose | 0.3 |
| Cationic guar gum | 0.3 |
| Cocoyl monoethanolamide | 0.5 |
| Dimethicone (polymerization degree: 2,000) | 0.5 |
| Dimethicone (polymerization degree: 200) | 0.5 |
| Malic acid | 0.7 |
| Benzyloxyethanol | 0.5 |
| Ethylene glycol distearate | 3.0 |
| Cocoyl benzalconium chloride | 0.5 |
| Glycerin | 1.0 |
| Sodium chloride | 0.2 |
| Deionized water | Balance |

The above-described shampoo (pH 3.7) was excellent in foam volume upon washing, and also good in foam lubricity upon washing and smoothness upon rinsing.

Example 10

Antidandruff Shampoo

|  | (wt. %) |
|---|---|
| Sodium POE(2) lauryl ether sulfate | 8.0 |
| Sodium lauryl sulfate | 4.5 |
| Myristyl alcohol | 1.0 |
| Cationic hydroxyethylcellulose | 0.1 |
| Cationic guar gum | 0.1 |
| Cocoyl monoethanolamide | 0.5 |
| Dimethicone (polymerization degree: 2,000) | 0.25 |
| Dimethicone (polymerization degree: 200) | 0.25 |
| Malic acid | 0.1 |
| Octopyrox | 0.5 |
| Ethylene glycol distearate | 2.0 |
| Polypropylene glycol (MW = 400) | 0.1 |
| Sodium chloride | 0.2 |
| Deionized water | Balance |

The above-described shampoo (pH 5.5) was excellent in foam volume upon washing, and also good in foam lubricity upon washing and smoothness upon rinsing.

The invention claimed is:

1. A hair cleansing composition comprising the following ingredients (A) to (E):
   (A) an anionic surfactant represented by the following formula (1) or (2):

   $$R^1O(CH_2CH_2O)_mSO_3M \quad (1)$$

   $$R^2OSO_3M \quad (2)$$

wherein $R^1$ represents an alkyl group having 10 to 18 carbon atoms, $R^2$ represents an alkyl group having 10 to 18 carbon atoms, M represents an alkali metal, alkaline earth metal, ammonium, alkanolamine or basic amino acid, and m stands for a number of from 1 to 5 in an amount of 10 to 22 wt % based on the weight of the hair cleansing composition,
   (B) myristyl alcohol in an amount of 0.05 to 5 wt % based on the weight of the hair cleansing composition,
   (C) a cationic polymer selected from the group consisting of cationic cellulose and cationic guar gum in an amount of 0.05 to 5 wt % based on the weight of the hair cleansing composition,
   (D) an organic acid selected from the group consisting of lactic acid and malic acid in an amount of 0.05 to 10 wt % based on the weight of the hair cleansing composition, and
   (E) benzyl alcohol in an amount of 0.5 to 5 wt % based on the weight of the hair cleansing composition
   wherein said hair cleansing composition has a pH of from 3 to 5.5 when diluted 20-fold by weight with water.

2. The hair cleansing composition to claim 1, wherein a content ratio by weight of said ingredient (A) to said ingredient (B) is from 10/1 to 40/1.

3. The hair cleansing composition according to claim 1, further comprising an amphoteric surfactant.

4. The hair cleansing composition according to claim 1, further comprising a silicone.

5. The hair cleansing composition according to claim 1, wherein said hair cleansing composition has a pH of from 3 to 4 when diluted 20-fold by weight with water.

6. The hair cleansing composition according to claim 1, wherein ingredient (C) is a cationic cellulose.

7. The hair cleansing composition according to claim 6, wherein the cationic cellulose is cationic hydroxyethylcellulose.

8. The hair cleansing composition according to claim 1, wherein ingredient (C) is a cationic guar gum.

9. The hair cleansing composition according to claim 1, wherein ingredient (C) is present in an amount of from 0.1 to 3 wt % based on the weight of the hair cleansing composition.

10. The hair cleansing composition according to claim 1, wherein ingredient (C) is present in an amount of from 0.3 to 1 wt % based on the weight of the hair cleansing composition.

11. The hair cleansing composition according to claim 1, wherein the amount of ingredient (B) is from 0.1 to 3 wt % based on the weight of the hair cleansing composition.

12. The hair cleansing composition according to claim 1, wherein the amount of ingredient (B) is from 0.5 to 2 wt % based on the weight of the hair cleansing composition.

13. The hair cleansing composition according to claim 1, wherein a content ratio by weight of said ingredient (B) to said ingredient (C) is from 10/1 to 10/10.

14. The hair cleansing composition according to claim 3, wherein the amphoteric surfactant is present in an amount of from 1 to 8 wt % based on the weight of the hair cleansing composition.

15. The hair cleansing composition according to claim 3, wherein the amphoteric surfactant is present in an amount of from 2 to 6 wt % based on the weight of the hair cleansing composition.

16. The hair cleansing composition according to claim 4, wherein the silicone is present in an amount of from 0.01 to 20 wt % based on the weight of the hair cleansing composition.

17. The hair cleansing composition according to claim 4, wherein the silicone is present in an amount of from 0.1 to 10 wt % based on the weight of the hair cleansing composition.

18. The hair cleansing composition according to claim 4, wherein the silicone is present in an amount of from 1 to 5 wt % based on the weight of the hair cleansing composition.

19. The hair cleansing composition according to claim 1, wherein the organic acid is present in an amount of 0.1 to 5 wt % based on the weight of the hair cleansing composition.

20. The hair cleansing composition according to claim 1, wherein the organic acid is present in an amount of 0.5 to 1 wt % based on the weight of the hair cleansing composition.

* * * * *